United States Patent
Pfanstiehl

[19]

[11] Patent Number: 6,088,116

[45] Date of Patent: Jul. 11, 2000

[54] QUALITY OF FINISH MEASUREMENT OPTICAL INSTRUMENT

[76] Inventor: John Pfanstiehl, 448 Harbor Dr. South, Indian Rocks Beach, Fla. 33785

[21] Appl. No.: 09/038,579

[22] Filed: Mar. 11, 1998

[51] Int. Cl.[7] .................................................. G01N 21/55
[52] U.S. Cl. ............................................................ 356/445
[58] Field of Search ................................... 356/445–448, 356/429, 73, 407, 419, 416, 328, 326

[56] References Cited

U.S. PATENT DOCUMENTS

| | | |
|---|---|---|
| 1,988,556 | 1/1935 | Hunter . |
| 2,311,101 | 2/1943 | Tuttle et al. . |
| 5,260,584 | 11/1993 | Popson et al. . |
| 5,377,000 | 12/1994 | Berends . |
| 5,401,977 | 3/1995 | Schwarz . |
| 5,805,291 | 9/1998 | Calvin et al. . |

OTHER PUBLICATIONS

Hunter; "The Glossmeter", Scientific Section, issued Apr. 1934, pp. 69–83.
Hunter; "A New Gloss Comparator"; Scientific Section, issued Oct. 1935 pp. 268–280.

Primary Examiner—K. P. Hantis
Attorney, Agent, or Firm—Gifford, Krass, Groh, Sprinkle, Anderson & Citkowski, PC

[57] ABSTRACT

A small battery powered instrument and method for measuring the finish appearance quality of highly reflective surfaces such as the paint on the exterior body panels of automotive vehicles. The instrument is placed on the surface to be measured; ambient light is prevented from entering from the interior space of the instrument by its opaque enclosure and by a seal which contacts the reflective surface. The user looks through a binocular viewing port at a reflection of a test object on the surface. The test object is illuminated by an internal bulb and internal power source which enables the instrument to be used in the field or with any ambient light levels. In the preferred embodiment, the test object is comprised of lines of alphanumeric characters; each line has successively smaller characters and the reflection is viewed at a fixed 20 degree angle to perpendicular to the surface. The measured value of the surface's finish appearance quality is the number of the line that has the smallest characters which are all clearly recognizable to the user. The instrument is comprised of a minimum number of optical components to make this measurement affordable to new markets. The alphanumeric characters provide a greater degree of precision in discerning small differences in finish appearance quality than test objects in the prior art.

27 Claims, 5 Drawing Sheets

QUALITY OF FINISH MEASUREMENT OPTICAL INSTRUMENT

BACKGROUND OF THE INVENTION

I. Field of the Invention

The present invention relates to instruments which measure surface finish appearance parameters of highly reflective surfaces such as automobile paint finishes.

II. Description of the Related Art

Smooth, highly reflective surfaces are found on many articles of manufacture because of their cosmetic appeal. Measurement of the perceived quality of appearance of such surfaces is highly desirable to enable setting and maintaining standards and to enable detection of small changes for the purpose of evaluating and improving the processes and materials used to make those surfaces.

Glossmeter Limitations:

Glossmeters, which measure the amount of light reflected off a surface, have been adequate for measuring surface finish parameters of surfaces such as concrete, rubber and wood which are minimally reflective. Glossmeters are also useful on moderately reflective surfaces such as file cabinets, other office furniture and Formica™. However, glossmeters are not sufficiently able to discriminate the levels of surface finish quality perceived by people on highly reflective surfaces such as the Class A finishes on the exterior body panels of automobiles. Because of this limitation, glossmeters are rarely if ever used by automotive dealerships, body shops, detailers or even by field representatives of refinish paint manufacturers.

One of the leading manufacturers of glossmeters, BYK-Gardner, makes a device called Micro-Haze which has added a second reflection haze scale to supplement its specular gloss readings. The device produces a beam of light which is reflected of the surface being measured, goes through an aperture and falls on photoelectric sensors. The gloss value is dependent on the input of sensors receiving light at a specular reflection angle from 19.1 to 20.9 degrees. The haze value is dependent on the light reflected at 1.8 degree range on both sides of the gloss angle. The outputs of its detectors are processed electronically to produce a reading from 1–180 gloss units on its own gloss scale and from 10–500 units on its Haze scale. The light received by an additional detector at a 45 degree angle can be used to perform a mathematical compensation on the haze value for variances in brightness levels.

Micro-Haze currently costs over $5,000 and is rarely if ever seen at body shops, dealerships, detailers or reconditioning centers. Micro-Haze provides more information about surface finish quality than glossmeters which do not produce haze measurement, but it is limited in its ability to measure what humans perceive when they are evaluating surface finish quality. BYK-Gardner's application literature states "The measurement of specular gloss and reflection haze does not take into account the visual impression of orange peel."

Visual-mechanical Devices:

Early attempts to measure the quality of appearance of surface finishes used a device known as the Glow Box™. This device is comprised of a metal light box, approximated 12 inches square, with bulbs inside and with four external supporting legs. A test object printed with ten rows of "C" shaped Landolt rings, each row a different height, is affixed to the underside of light of light box and the light box is then set on its legs on a reflective surface. The user moves around the Glow Box looking at the reflection of the test object to determine which row has the smallest "C" shaped rings that don't appear as a closed circle. Ambient light also reflects off the surface being measured and therefore the Glow Box can only be used in darkened rooms and it can't be used outside during daylight. Furthermore, neither the angle with which the viewer sees the reflection, nor the distance the user is from the surface is controlled. Repeatability therefore can be a problem. The Glow Box is neither small, nor portable; it requires 120-volt power for the light source.

The present invention can be used outside or inside under any lighting conditions; the Glow Box cannot. In addition the present invention reflects light off the surface at a fixed angle while the Glow Box angle of reflection can change from minute to minute or from user to user. The present invention is battery powered enabling it to be used in the field. The Glow Box requires a 120 v power cord. The present invention has a compact, lightweight plastic enclosure which is easy to transport and store, and is less likely to damage high quality painted surfaces during normal use if dropped. In comparison, the Glow Box is a 12 inch by 12 inch metal box supported by four metal legs.

Japanese automotive manufacturers are reported to have used a PGD meter at one time for evaluating finish quality. The PGD meter is a relatively complicated and expensive instrument. It employs an optical system which bounces light off four internal mirrors and requires magnification in the viewing tube. Its operation further requires a variable resistor and voltmeter to keep the light source in a limited range of illumination. Another serious drawback is its use of a 55-degree angle of reflection. Angles of that magnitude are primarily suitable for finishes with low to moderate reflective qualities and are not sufficiently discriminating with highly reflective finishes.

The present invention is considerably less expensive and less complicated than the PGD meter which has four internal mirrors and a magnifying eyepiece. The present invention has no mirrors, no magnification, and no eyepiece. The PGD meter is limited to monocular vision; the present invention has the preferable binocular vision. The PGD meter uses a 55 degree reflection angle. The 20 degree angle of the preferred embodiment of the present invention is much better suited to measurements on highly reflective surfaces.

A Tension instrument was tested by at least two paint manufacturers in the past for its ability to evaluating highly reflective finishes on automobiles but is not commonly in use in the US today. Tension employs a test object comprised of a grid pattern in which the lines become progressively smaller and closer together. It is a large instrument which has a viewing port designed to hold an instant developing film camera to take a photograph of the test object's reflection on the surface being measured. After the photograph of the reflection is taken, the photograph is examined to determine the smallest lines which can be discerned as being visually distinct from each other. The number assigned to the smallest visible lines is the measurement value.

A disadvantage of Tension is that the resolution and consistency of instant developing film is relatively poor and that affects repeatability and reproducibility. The cost and problems associated with instant developing film are therefore another disadvantage. One paint manufacturer found it necessary to use only fresh film bought directly in case lots from the manufacturer. Tension is not a commonly used instrument in the automotive refinish industry and is seldom if ever seen in the automotive field testing.

The Tension meter requires the use and expense of an instant developing camera and film. The present invention requires no camera, no film, and no subsequent manual measurements and calculation. In addition, the preferred embodiment of present invention uses a test object which is far more discriminating than the linear grid pattern used in Tension.

Electro-optical Devices:

Although the above referenced prior art has not solved the problem of adequate field measuring of the quality of surface finish, the need for measurement of this parameter by automobile manufacturers is very strong. Currently expensive electronic instruments made by ATI and Autospect are in use in automotive factories in the US.

One of the earliest electro-optical instruments designed to measure appearance quality of surface finishes was the Hunter Dorigon instrument. A light source produced a beam of light which is reflected of the surface being measured to an optical sensor at a 30 degree specular angle. A slit was positioned 3/10ths of a degree from the 30 degree position. The amount of light it received at these two locations was compared and processed by a computer to produce a numerical value. The Hunter Dorigon instrument is large, complex, and costly. It is rarely if ever used outside of laboratory applications and it is no longer being produced or serviced by Hunter.

ATI's Model 1864 SQC Portable Appearance Data Collector costs approximately $16,000. ATI's sales brochure describes its operation as follows: "During operation, a controlled beam of light is projected through an opening onto the test specimen. The reflected portion of the light beam passes through a rotating eight bladed disc and is focused upon the lens at the aperture. As the blades pass through the light beam, the silhouetted image of the blades moves across the detector slit causing a large increase in light flux to be present at the photo detector. This detector converts the light to an electronic signal that is later processed by a microprocessor and is displayed in D.O.I./Gloss values."

Autospect's QMS-BP Quality Measurement System is even larger then ATI's 1864 system. The system includes a high gloss sensor, a low gloss sensor, a processor, a battery charger, VGA monitor, keyboard, printer, three batteries and an AC power module. It uses a complex photoelectric system and microprocessor to covert reflected light to its own 0 to 100 scale.

Autospect's QMS-I system has an inspection arch mounted over an automobile assemble line. As a vehicle passes through the arch, information is acquired from the plant's network regarding the VIN, color, style etc. Autospect sales literature states: "At predetermined positions, the cameras take pictures of the light reflected from the vehicle's surface. The images are digitized and analyzed by Autospect's specialized software."

The high price and complexity alone are enough to preclude the prior art electronic surface finish appearance instruments from being used by automotive dealerships, detailers and body shops. In addition, there is growing concern that the measurement numbers produced by even the most expensive and complex surface finish appearance instruments may not correlate well with human perception of the quality of appearance of high gloss surfaces. The ASTM, American Society for Testing and Materials, has formed a sub-committee to examine the psycho-physics of human perception of surface finish quality in order to develop methodology and measurements in this field which accurately correlate with human perception.

In spite of the strong economic need to measure the appearance quality of highly reflective surface finishes such as on automotive exterior body panels, the prior art, including both visual-mechanical and electro-optical, has not produced a relatively low-cost instrument which satisfies this need. This is evident by the fact that instruments for measuring finish appearance quality are virtually unknown at automotive dealerships, body shops, and detailers.

The present invention overcomes all the limitations of the prior art. The present invention not only costs considerably less than glossmeters, it measures "distinction of image-gloss" which more closely correlates to human perception of finish appearance quality on highly reflective surfaces.

SUMMARY OF THE INVENTION

The present invention is a small battery powered instrument which measures the finish appearance quality of highly reflective surfaces such as the paint on the exterior body panels of automotive vehicles. The user places the instrument on the surface to be measured; ambient light is prevented from entering from the interior space of the instrument by its opaque enclosure and by a soft seal on the bottom surface. The user positions their eyes at the binocular viewing port and pushes a switch which electrically connects an internal light to the internal power source. The light illuminates a test object whose reflection is seen on the surface being measured. In the preferred embodiment, the test object is comprised of rows of alphanumeric characters; each row has successively smaller characters. The reading is obtained by the user determining which row has the smallest characters which are all clearly recognizable. The number adjacent to the row is the measured value of the surface's finish appearance quality.

The self-contained power source enables the instrument to be conveniently used in any location, in the laboratory or in the field. The present invention reduces the number of optical components to the bare minimum which are essential to successfully discriminate finish appearance quality on Class A finishes and thereby provided the first affordable field-use instrument for this task. The opaque enclosure and the soft seal prevent entry of ambient light and thereby enable it to be used in all conditions from bright sunlight to total darkness.

An additional advantage of the present invention is that it also provides for the preferred binocular viewing. A still further advantage of the present invention is that the alphanumeric characters in the present invention provide a far greater degree of precision in discerning small differences in finish appearance quality than test objects used in the prior art.

Other advantages and features of the present invention will be come more apparent from the following detailed description when read in conjunction with the accompanying drawing.

BRIEF DESCRIPTION OF THE DRAWING

The present invention will be more fully understood by reference to the following detailed description of the preferred embodiment of the present invention when read in conjunction with the accompanying drawing, in which like reference characters refer to like parts through the views, and in which.

DETAILED DESCRIPTION OF THE PREFERRED EMBODIMENT

Figure 1:
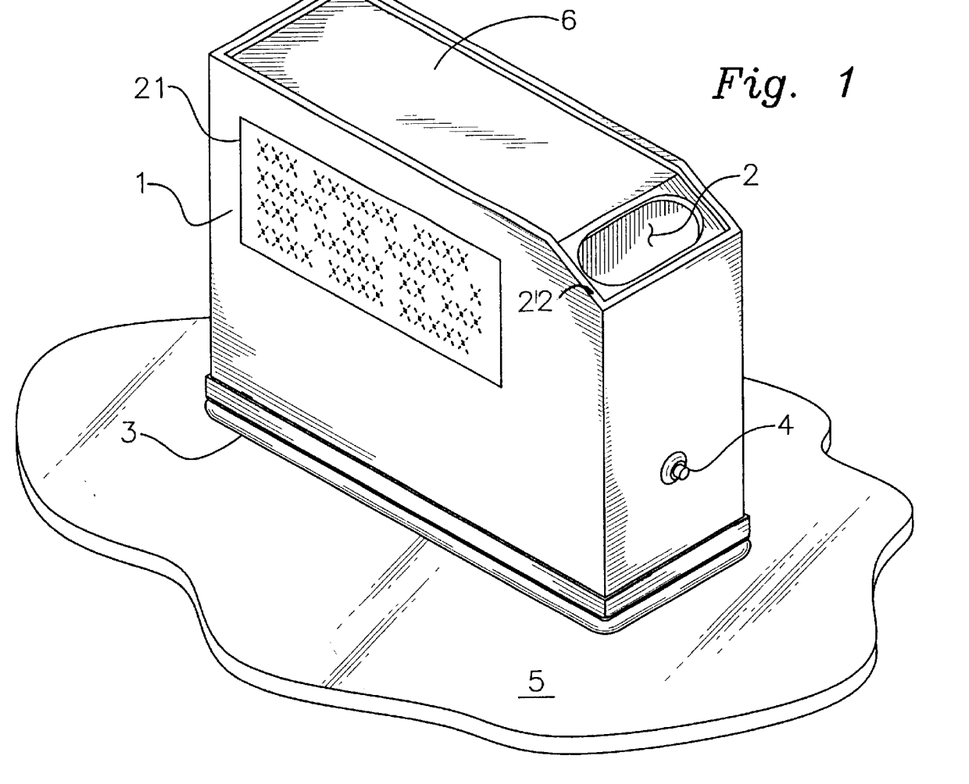
FIG. 1 is a perspective view of the present invention being used to measure a surface.

FIG. 1 shows the present invention in use. Enclosure 1 is placed upon a highly reflective surface 5, contact being made by the flexible seal 3. The user presses switch 4 and looks with both eyes in through viewing port 2 in roof 6.

Instruction summary label 21 is affixed to the enclosure 1 to provide essential information about operation which could be lost or forgotten if only found in an instruction manual. For example "Look at the reflection of the target on the finish and record the smallest line in which all characters can be read with certainty." If one user records the smallest line which can be read with certainty but later forgot the "with certainty" portion of the instruction and began recording the smallest line which could be read with almost certainty, the readings would not be as comparable. Placing the essential instructions on the instrument reduces the chance that they will be remembered inaccurately.

Figure 2:
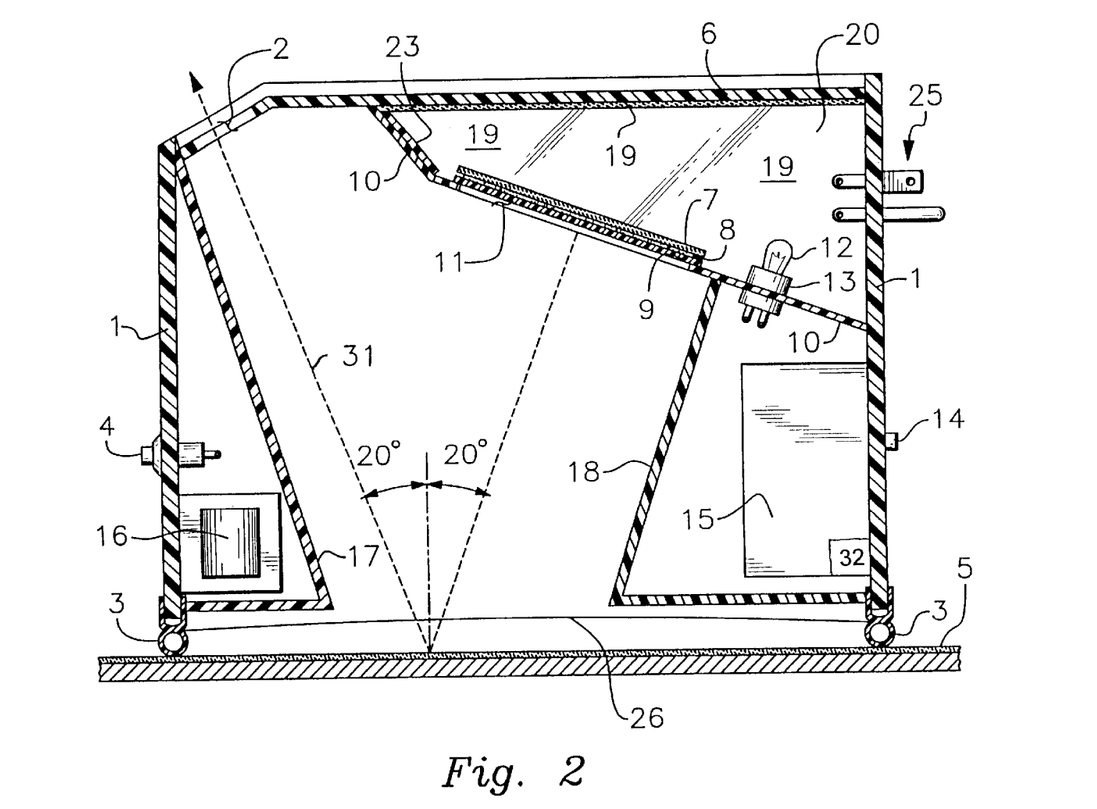
FIG. 2 is a cut-away side elevational view of the present invention.

FIG. 2 shows a cross section of the instrument; the electrical wires are omitted for clarity. Switch 4 electrically connects power source 15 to light up bulb 12. Bulb 12 is in a sealed light chamber 20 whose walls are comprised of the upper portion of enclosure 1, roof 6, and test object support 10. Bulb 12 is typically a small high intensity bulb such as a halogen bulb. Reflective coating 19 is applied to the light chamber walls to minimize light absorption and thereby provide the most light with the minimum power and thereby minimize battery drain. Test object 8 is sandwiched between lower support plate 9 and diffuser plate 7. Test object 8 is located over opening 11 in test object support 10. Light passing though test object 8 is reflected off surface 5 to viewing port 2. Dashed line 31 indicates the line of sight of the reflection of the test object 8. This line of sight 31 is generally perpendicular to viewing port 2. The angle between the light of the test object reflection seen through viewing port 2 makes a 20 degree angle to the perpendicular from surface 5. Baffles 17 and 18 cover transformer 16 and power source 15 respectively, minimizing visual distraction from the test object and enhancing the cosmetic appearance of the interior of the instrument.

Switch 4 is a low force push button switch which only is closed when pushed in to prevent the bulb from inadvertently remaining on after the instrument is used. To facilitate ease of viewing and fix the angle of viewing, the exterior surface 22 of enclosure 1 adjacent to viewing port 2 is perpendicular to the reflected light.

In the preferred embodiment, reflective coating 19 is reflective pressure sensitive adhesive tape which can be easily applied to the interior walls of light chamber 20. Reflective tape reduces light absorption and eliminates the over spray, masking, expense, drying time, and pollution caused by spraying coatings.

The light output of the chamber is adjusted by applying non-reflective coating 23 comprised of non-reflective tape or flat black paint. Consistency in light chamber output between instruments is desirable for making measurements reproducible. Light output can also be adjusted by use of a variable resistor, constant voltage circuit, or adjustable feedback circuit with light sensor.

Enclosure 1 is made of opaque plastic materials to reduce weight and cost and to minimize damage to high quality surfaces if it is accidentally dropped or otherwise inadvertently contacts such surfaces. Baffles 17 and 18 are also made of opaque plastics. Plastics are well suited for these applications because they are easy to cut, bend and mold, and they are corrosion resistant which is an advantage in field-use instruments. Roof 6 is bent to conform with the angle of the exterior surface 22 of enclosure 1 adjacent to viewing port 2 and baffle 17 fits between enclosure 1 and roof 6 to eliminate the gap created when the length of roof 6 was shortened by said bend.

A second embodiment of the present invention is comprised of an enclosure and baffles made of collapsible materials such as bellows to permit the instrument to be collapsed when not in use for ease of storage and transportation.

Transformer 16 and power source 15 are located at the opposite ends of the enclosure to proved a balanced weight and feel to the instrument. Power source 15 includes a charge/recharge system which is activated by pressing button 14 when plug 25 is connected to an extension cord. The charging system includes a battery conditioning system 32 that automatically drains the rechargeable batteries, charges them to full capacity and then turns itself off. The instrument can be left connected to the extension cord without overcharging the batteries. Use of rechargeable batteries and frequent recharging maintains the power source voltage at a relatively constant level which thereby produces a relatively constant level of light output from the light chamber.

Figure 1A:
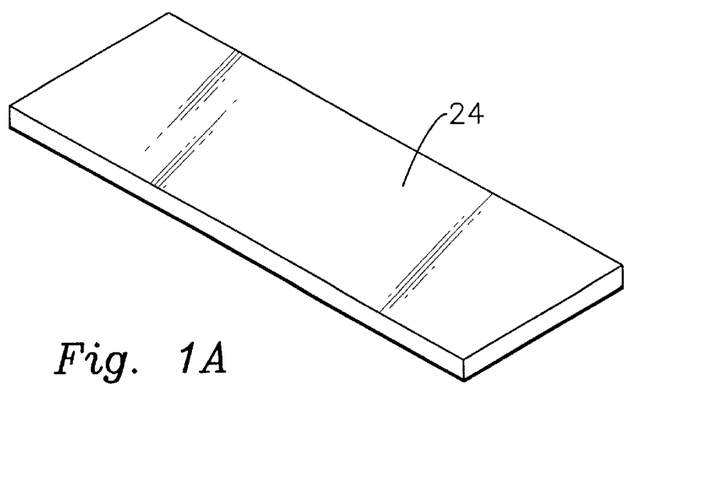
FIG. 1A is perspective view of a mirror provided with the present invention.

The visual acuity of the user of the present invention can be checked by placing the present invention upon mirror 24. If the user can read the smallest line reflected in the mirror, the user's visual acuity is sufficient for use of the instrument without correcting their vision. Mirror 24 is shown as separate from the instrument but it can be attached inside the enclosure by means of a hinge which permits it to be lowered for visual acuity tests or placed in an up position for surface finish measurements. An internal hinged mirror can also be made to block entry of dirt and dust to the interior of the instrument when not in use.

If the user can't see the smallest line, use of "magnifiers," the inexpensive eye glasses found in drug stores, correct vision sufficiently for a majority of users. In addition, a mathematical correction can be used to normalize data taken by a user with a known level of visual acuity.

A lens adapter may be provided and permits magnifying or correcting lenses to be removably installed in the viewing port. A camera adapter may also be provided and enables a camera to be attached to produce hard copy documentation of the finish appearance quality.

Seal 3 is attached by sliding onto the walls of enclosure 1. The sealing surface is comprised of soft rubber which conforms to various curvatures and accent lines found on exterior automotive body panels. In addition, lower edge 26 of enclosure 1 is machined to be slightly concave. This permits seal 3 to accommodate a greater degree of convex curvature on a panel. This is desirable in automotive applications because the majority of curved exterior body panels are convex, and few are concave.

Diffuser 7 eliminates the sharp shadows or reflections of the light chamber and thereby provides a more uniform illumination of test object 8. Lower support plate 9 is made out of high quality non-glare transparent plastic material to further reduce unwanted reflections.

Figure 3:
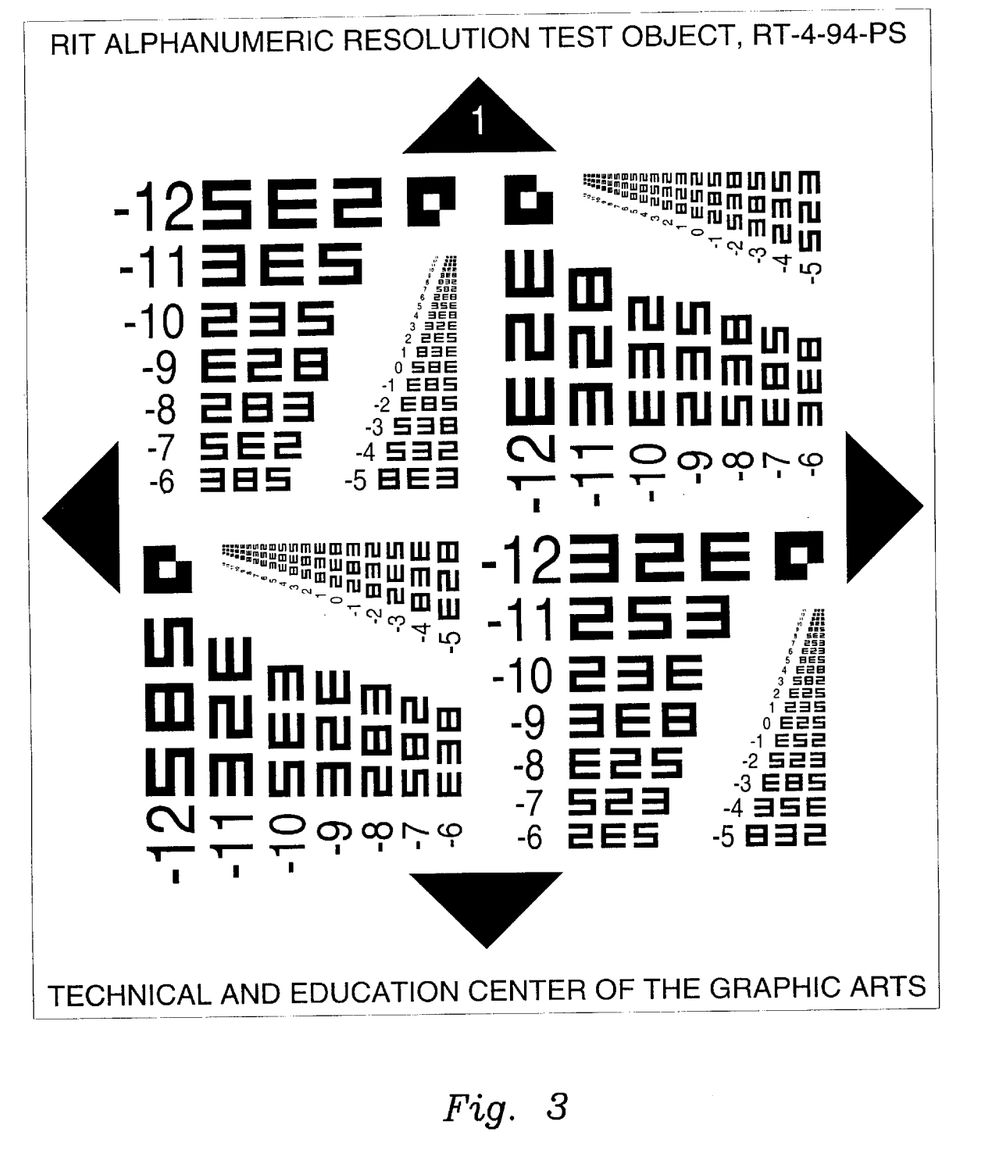
FIG. 3 is RIT Alphanumeric Resolution Test Object RT-4-94-PS.
Figure 4:
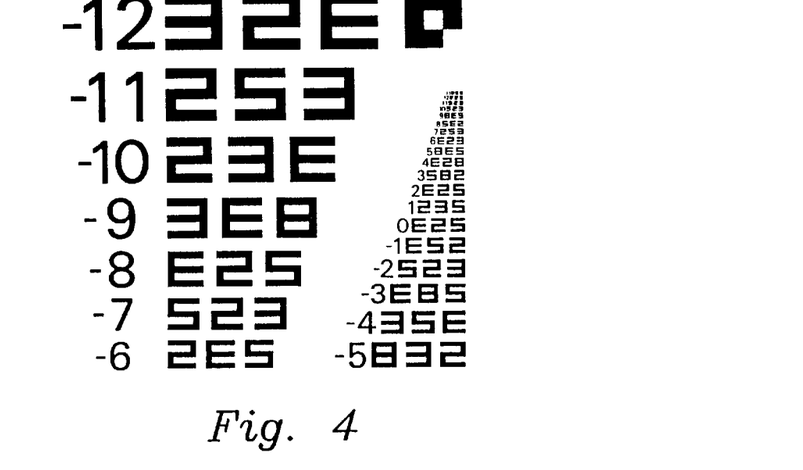
FIG. 4 is an improved smaller test object.

Test object 8 is comprised of rows of alphanumeric characters such as shown in RIT Alphanumeric Resolution test Object, RT-4-94-PS shown in FIG 3. Proprietary testing has shown that RIT alphanumeric test object style characters are far superior to any test object used in the prior art. However, RIT's original test object is too large for a small hand-held instrument. One embodiment of the present invention uses a substantially smaller test object shown in FIG. 4. The requirements of surface finish appearance quality measurements, in combination with the design of the alphanumeric characters, eliminates the need for the four separate orientations of the characters shown in FIG. 3.

Figure 5:
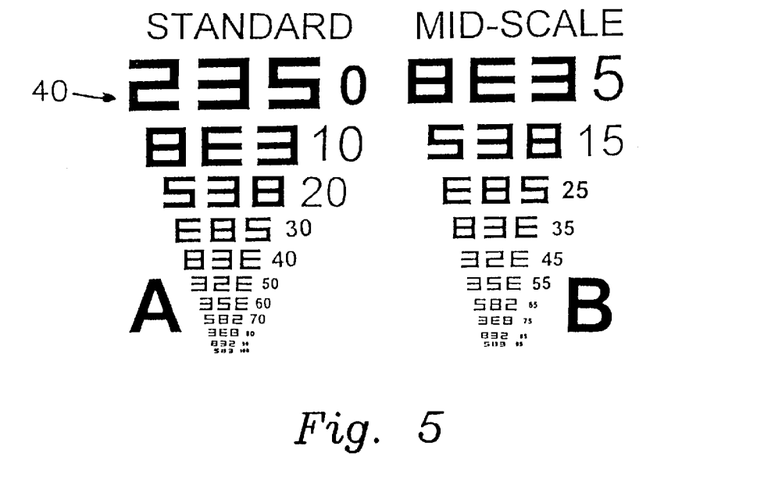
FIG. 5 is a further improved test object.
Figure 6:
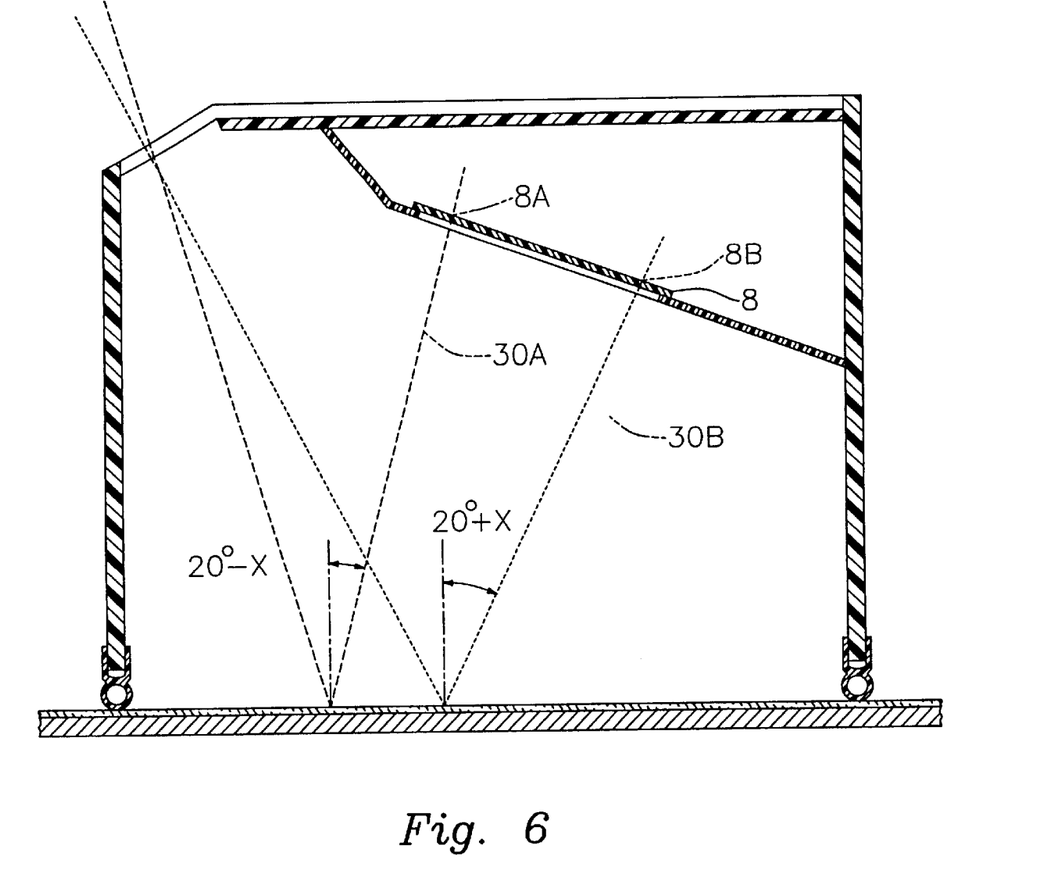
FIG. 6 is a simplified perspective view of the invention.

The present invention uses a different test object, FIG. 5, for general automotive use. As shown, this test object includes alphanumeric characters 40 that are rectangular block elements. One advantage of this novel test object is that the largest characters are located at the top of the pattern and the smallest characters are at the bottom of the pattern. With reference to FIG. 6, the advantages of this novel test object are shown. The reflection of the largest characters 8A, as shown by line of sight 30A, in this test object will be at an angle closer to perpendicular to the surface being measured (20 degrees+X degrees) and the smallest characters 8B, as shown by line of sight 30B, will be reflected at an angle farther from perpendicular (20 degrees–X degrees). This expands the range of the test object due to the fact that less reflective surfaces have greater ability to produce clear reflections as the angle of reflection increases from the perpendicular. Conversely, more reflective surfaces are required to produce clear reflected images as the angle of reflection approaches perpendicular to the surface. This phenomenon can be witnessed by looking at the reflection of a magazine on a relatively poorly reflective surface such as a file cabinet. The farther the reflection angle is from the perpendicular, the clearer the reflected image appears.

Another advantage of the test object is a numbering system which is simpler to read and understand. The scale runs from 100 to 0; 100 is the best finish appearance quality and no negative numbers are used. The RIT test object goes from –12 through 0 to 13.

Another advantage is separating the character lines into two columns. The height of characters differs only about 12% from one line to another in the RIT test object. Placing every other line from the RIT test object into column A creates a column with lines whose characters differ in height by approximately 25% from one line to the next. This makes it faster and easier for a technician to determine which line is the smallest one that is clearly visible on a given surface and provides an appropriate amount of resolution for general automotive applications. However by making column B from mid-level lines which are 12% smaller than the lines in column A, the technician does not sacrifice resolution for ease of use. Technicians can use column B for the added resolution whenever it is required. An additional advantage is labeling the scales with titles "Standard" and "Mid-Level" on the top of the columns and with "A" and "B" to provide clearer instructions for demonstrations to first-time users.

Another advantage of the test object is realized by placing the line number to the left of the character line. The technician can therefore concentrate on reading the characters and need only look over to see the line number after the appropriate line is chosen.

Another advantage of the test object is realized by placing the lines of characters which are most frequently used in a column on the left side and by positioning the largest characters at the top. Technicians therefore begin reading the pattern in the same manner as they would read text on a page, from left to right and from the top down. The RIT pattern requires that the technician switch from the large column to the small column and switch from reading down to reading up as they move from line -6 to line -5 to line -4.

Another embodiment of the present invention has means to enable movement of test object 8 with respect to support 10 thereby keeping the test object characters which the user is viewing at a constant reflection angle.

A summary of the use of the present invention is as follows. The technician places rubber seal 3 of enclosure 1 on reflective surface 5. The technician pushes switch 4 and looks through viewing port 2 in roof 6 to view the reflection of test object 8 which is illuminated by lamp 12. After a studied decision, the technician records the row number of the smallest alphanumeric characters on the test object which can be read with certainty. The row number is the measurement value of the surface finish quality of the reflective surface.

Having described my invention, however, many modifications thereto will become apparent to those skilled in the art to which it pertains without any deviation from the spirit of the invention as defined by the scope of the appended claims.

I claim:

1. A portable self-contained field-use instrument for measuring surface finish parameters of a highly reflective surface to determine the distinctness of image of the surface comprising:

an opaque enclosure which blocks the majority of ambient light from illuminating a portion to be measured of said reflective surface when said instrument is placed upon said reflective surface;

a light source contained within said enclosure;

a single test object for measuring said distinctness of image gloss of said surface contained within said enclosure; and a binocular viewing port on the exterior of said enclosure for viewing a reflection of said test object illuminated by said light source when said instrument is placed upon said reflective surface;

said test object and said viewing port positioned to produce a predominantly fixed specular reflection angle for viewing said reflection of said test object on said surface.

2. The invention as defined in claim 1, said light source comprising a bulb and battery power source contained within said enclosure.

3. The invention as defined in claim 2, said battery power source comprising rechargeable batteries and a charging system.

4. The invention as defined in claim 3, wherein said charging system is further comprised of a battery conditioning system and automatic shut-off.

5. The invention as defined in claim 2, said battery power source further comprising a constant voltage power source.

6. The invention as defined in claim 2, further comprising a light sensor and feedback loop to said battery power source to maintain a constant light level from said light source.

7. The invention as defined in claim 1, wherein said light source is further comprising a light chamber;

said light chamber comprising reflective and non-reflective coatings on the interior walls of said light chamber whereby increasing the amount of said non-reflective coatings adjusts the light level of said light chamber to produce a uniform light level from one of said instruments to another of said instruments.

8. The invention as defined in claim 1, further comprising a flexible seal attached to said enclosure and contacts said reflective surface.

9. The invention as defined in claim 8, said enclosure further comprising a concave edge where said flexible seal is attached.

10. The invention as defined in claim 1, wherein said viewing port is binocular.

11. The invention as defined in claim 1, wherein the exterior surface of said viewing port is fixed to said enclosure parallel to the user's eyes and is perpendicular to the line of sight of said reflection of said test object.

12. The invention as defined in claim 3, wherein said rechargeable batteries and said charging system of said battery power source are placed at locations within said enclosure to distribute their weight evenly.

13. The invention as defined in claim 1, further comprising a normally open switch to turn on said light source.

14. The invention as defined in claim 1, wherein said test object comprises sets of alphanumeric characters of multiple sizes.

15. The invention as defined in claim 14, wherein said alphanumeric characters are comprised of rectangular block elements.

16. The invention as defined in claim 14, wherein said sets of alphanumeric character are arranged in one or more columns;

said columns having the sets of the largest of said of characters at one end;

said sets comprised of progressively smaller of said characters arranged in descending order;

said set comprised of the smallest characters at the other end of said columns;

said columns having sets of alphanumeric characters whose size is at mid-levels between the size of sets of characters in adjacent columns whereby the user of said instrument only needs to examine said alphanumeric characters in one column to obtain a standard measurement but can examine said adjacent columns when a measurement which has a greater degree of resolution is needed.

17. The invention as defined in claim 16, wherein the largest of said sets of alphanumeric characters are located at the top of said columns whereby the reflection angle of said largest set of said characters is at a greater angle to perpendicular to said surface than set of smallest characters the effect of which expands the range of surface finishes which can be measured by said sets of alphanumeric characters.

18. The invention as defined in claim 14, wherein said sets of alphanumeric characters are further comprised of a particular identification number for each of said sets;

said particular identification numbers being from 0 to 100;

said particular identification number 100 located with the set of smallest alphanumeric characters whereby the rating of surface finish quality is easily understandable.

19. The invention as defined in claim 14, wherein said sets of alphanumeric characters are further comprised of identification characters located to the right of said set whereby the user of said instrument can concentrate on viewing said alphanumeric characters and need look at said identification characters only after choosing the smallest of said sets of alphanumeric characters in which all characters can be read with certainty.

20. The invention as defined in claim 1, comprising: a diffuser between said light and said test object.

21. The invention as defined in claim 1, comprising: a lens holder on said viewing port for supporting a removably attachable magnifier lens.

22. The invention as defined in claim 1, comprising:

a camera holder on said viewing port for supporting a removably attachable camera to produce hard copy documentation of the measurement on a particular surface.

23. The invention as defined in claim 1, wherein said enclosure is collapsible.

24. The invention as defined in claim 1, wherein said fixed specular reflection angle is approximately 20 degrees from perpendicular to said reflective surface.

25. The invention as defined in claim 1, wherein said test object is moveable within said enclosure.

26. A method for measuring surface finish parameters of a reflective surface to determine the distinctness of image gloss of the surface comprising the steps of:

placing a self-contained and completely enclosed portable instrument on said surface; wherein said instrument blocks out ambient light;

illuminating a light source within said instrument;

projecting a single test image comprised of alphanumeric characters of multiple sizes illuminated by said light source upon said surface;

looking through a viewing port of said instrument to view the reflection of said projected test object upon said surface;

determining the smallest of said alphanumeric characters in said reflection of said projected test object which can be read with certainty;

obtaining a measurement of the quality of the surface finish of said surface by noting the rating which identifies the smallest of said alphanumeric characters in said reflection of said projected test object which can be read with certainty.

27. A portable self-contained instrument for measuring surface finish parameters of a highly reflective surface to determine distinctness of image gloss of the surface finish comprising:

an opaque enclosure for blocking the majority of ambient light from illuminating a portion of said reflective surface to be measured when said instrument is placed upon said reflective surface;

a light source contained within said enclosure;

a test object of sufficiently small dimensions for containment within said enclosure of said portable instrument;

said test object including one or more alphanumeric characters;

a viewing port on the exterior of said enclosure for viewing a reflection of said test object illuminated by said light source upon said highly reflective surface when said instrument is placed upon said reflective surface; and said test object and said viewing port being positioned to produce a predominantly fixed specular reflection angle of 20 degrees to the perpendicular to said surface when the user looks through said viewing port to view said reflection of said test object on said surface;

wherein said fixed specular reflection angle provides objective means for obtaining repeatability of said surface finish measurements from user to user and from day to day.

* * * * *